United States Patent [19]

Cottone, Jr.

[11] Patent Number: 5,250,073
[45] Date of Patent: Oct. 5, 1993

[54] TORQUEABLE AND FORMABLE BIOPSY FORCEPS

[75] Inventor: Robert J. Cottone, Jr., Fort Lauderdale, Fla.

[73] Assignee: Cordis Corporation, Miami, Fla.

[21] Appl. No.: 896,621

[22] Filed: Jun. 10, 1992

[51] Int. Cl.⁵ ............................................. A61B 10/00
[52] U.S. Cl. ..................................... 606/206; 128/751
[58] Field of Search ............... 128/749, 751, 754, 657, 128/772; 606/205, 206

[56] References Cited

U.S. PATENT DOCUMENTS

| | | | |
|---|---|---|---|
| 2,790,437 | 4/1957 | Moore | 128/751 |
| 4,721,117 | 1/1988 | Mar et al. | 128/772 |
| 4,763,668 | 8/1988 | Macek et al. | 606/206 |
| 4,966,163 | 10/1990 | Kraus et al. | 128/772 |
| 5,147,380 | 9/1992 | Hernandez et al. | 128/751 |

*Primary Examiner*—Max Hindenburg
*Attorney, Agent, or Firm*—Tarolli, Sundheim & Covell

[57] ABSTRACT

A biopsy forceps device is provided exhibiting improved torqueable and formable characteristics. The device includes a handle and a core wire connected at its proximal end to the handle and connected at its distal end to a forceps assembly. The control wire displacing device is carried by the handle and serves to displace the core wire for moving the core wire between a forceps open position and a forceps closed position. The core wire includes at least three elongated portions including a proximal portion having a proximal end secured to the wire displacing means, a distal portion having a distal end secured to the forceps assembly and an intermediate portion located between the proximal and distal portions. The proximal portion is of greater length than either the intermediate or distal portions and is of greater diameter than the intermediate portion which, in turn, is of greater diameter than the distal portion. The first tapered portion is located between the distal portion and the intermediate portion and a second tapered portion is located between the intermediate portion and the proximal portion.

15 Claims, 6 Drawing Sheets

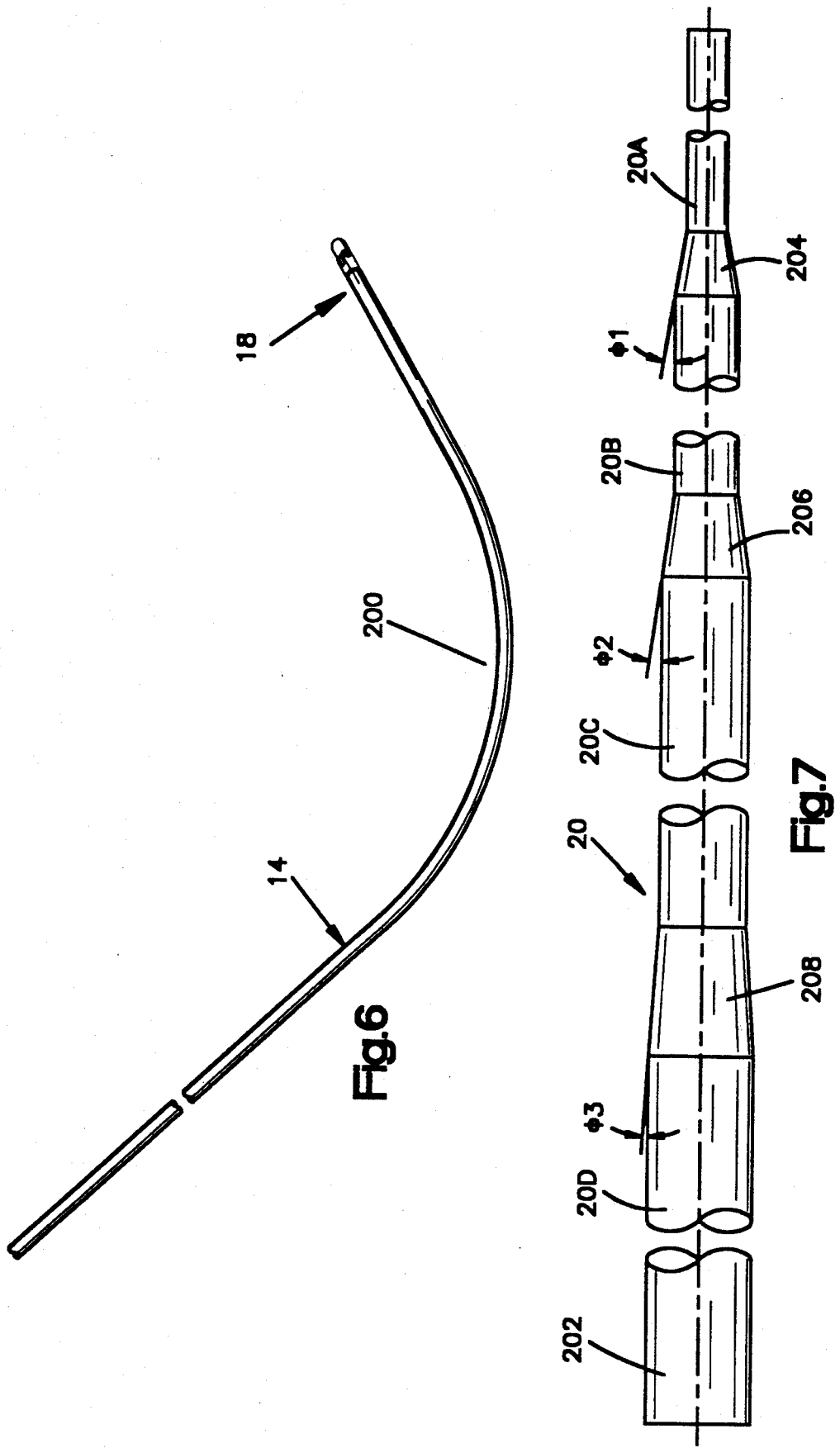

TORQUEABLE AND FORMABLE BIOPSY FORCEPS

FIELD OF THE INVENTION

The present invention relates to biopsy forceps and, more particularly, to a biopsy forceps device having improved torqueable and formable characteristics.

DESCRIPTION OF THE PRIOR ART

Biopsy forceps are known in the art and are in wide use for purposes of obtaining a tissue sample. One example of the prior art takes the form of the U.S. Pat. No. to J. P. Clossick, 4,815,476, assigned to the same assignee as the present invention. Such a forceps device includes a handle assembly slidably mounting a trigger member thereon and an elongated coil spring guide connected to the handle assembly at the proximal end of the guide. A pair of forceps are mounted to the distal end of the guide and a stylet-control wire received within the lumen of the guide is connected at its proximal end to the trigger and at its distal end to the pair of forceps.

A guide sheath may be introduced into a patient's body vessel, such as an artery, and the distal end of the forceps device is introduced into the sheath and guided to the site of interest. The handle assembly remains outside of the patient's body allowing the attending physician to operate the trigger. Forward movement of the trigger causes the stylet-control wire to move the forceps to an open position and rearward movement of the trigger causes the pair of forceps to move to a closed position to capture a tissue sample therebetween. The forceps device is then removed from the guide sheath so that the captured tissue sample may be examined.

In use, such a biopsy forceps device is employed by a physician and introduced into a patient's body, such as into a heart, to obtain a biopsy tissue sample. As such, the control wire, sometimes referred to as the core wire, must exhibit characteristics that permit the physician to push the biopsy device into a heart cavity while traversing various bends enroute to the site of interest. As the device is maneuvered into and toward the site of interest, the physician twists the handle, external of the human body, to transmit torque to the core wire. Consequently, the proximal end of the core wire needs to be sufficiently rigid to exhibit the desired torque and pushability characteristics to deliver the forceps assembly to the desired site. At the same time, however, the distal end of the core wire should exhibit sufficient flexibility and formable characteristics to deter or minimize the chance for perforation of a vessel or heart wall as the core wire is advanced into the patient's body. Moreover, it is frequently desired that the core wire and its surrounding guide be formed with a preset curve in the area approaching the distal end of the core wire. The shape should exhibit the most optimal curve in which a physician may gain access through the RA crossing the tricuspid valve, transverse RV to the septum wall biopsy site. Moreover, it is desirable that the distal end be sufficiently formable to permit the physician to increase or decrease the curvature of the preset curve.

In the prior art, it is known to provide a control wire means or core wire having a length on the order of 32.5 inches wherein the core wire is made of solid stainless steel having a uniform diameter throughout its length and with the diameter being chosen to provide a compromise between the desired pushability and torque characteristics and the desired formability and flexibility characteristics. Some physicians prefer a relatively large diameter core wire because it exhibits maximum pushability and torque characteristics, while other prefer a much narrower diameter that will offer greater flexibility and formable characteristics at the distal end thereof.

The present invention is directed toward satisfying the foregoing needs by providing a core wire which is divided into at least three portions which presents greater pushability and torque characteristics near the proximal end of the core wire while offering greater formability and flexibility characteristics near the distal end of the core wire.

SUMMARY OF THE INVENTION

In accordance with the present invention, it is contemplated that the improved core wire be employed with a biopsy forceps device which includes a handle, an elongated flexible hollow-body portion, such a coil spring, having a lumen extending therethrough, and having a proximal end and a distal end. A forceps assembly is coupled to the distal end of the body portion and the assembly includes a pair of forceps. A control wire, or core wire, having proximal and distal ends extends through the lumen in the body portion and is coupled at its proximal end to the handle and at its distal end to the forceps assembly. A core wire displacing means is carried by the handle and is movable between first and second positions for respectively moving the core wire between a forceps open position and a forceps closed position.

The improved core wire includes an elongated metal rod having at least three portions including a proximal portion having a proximal end secured to the wire displacing means carried by the handle, a distal portion having a distal end secured to the forceps assembly and an intermediate portion located intermediate the proximal and distal portions. The proximal portion is of greater length than either the intermediate or distal portions. Also, the proximal portion is of greater diameter than the intermediate portion and which, in turn, is of greater diameter than the distal portion. A first tapered portion is located between the distal portion and the intermediate portion and a second tapered portion is located intermediate the intermediate portion and the proximal portions. These tapered portions each have a taper that tapers inwardly in the distal direction.

BRIEF DESCRIPTION OF THE DRAWINGS

The foregoing and other objects of the invention will become more readily apparent from the following description of the preferred embodiment of the invention as taken in conjunction with the accompanying drawings which are a part hereof and wherein:

FIG. 6 is an exploded view showing a portion of the length of the coil spring guide which near its distal end is provided with a preset curve; and FIG. 7 is an enlarged fragmentary view illustrating the control wire or core wire in accordance with the present invention.

DESCRIPTION OF THE PREFERRED EMBODIMENT

Figure 3:
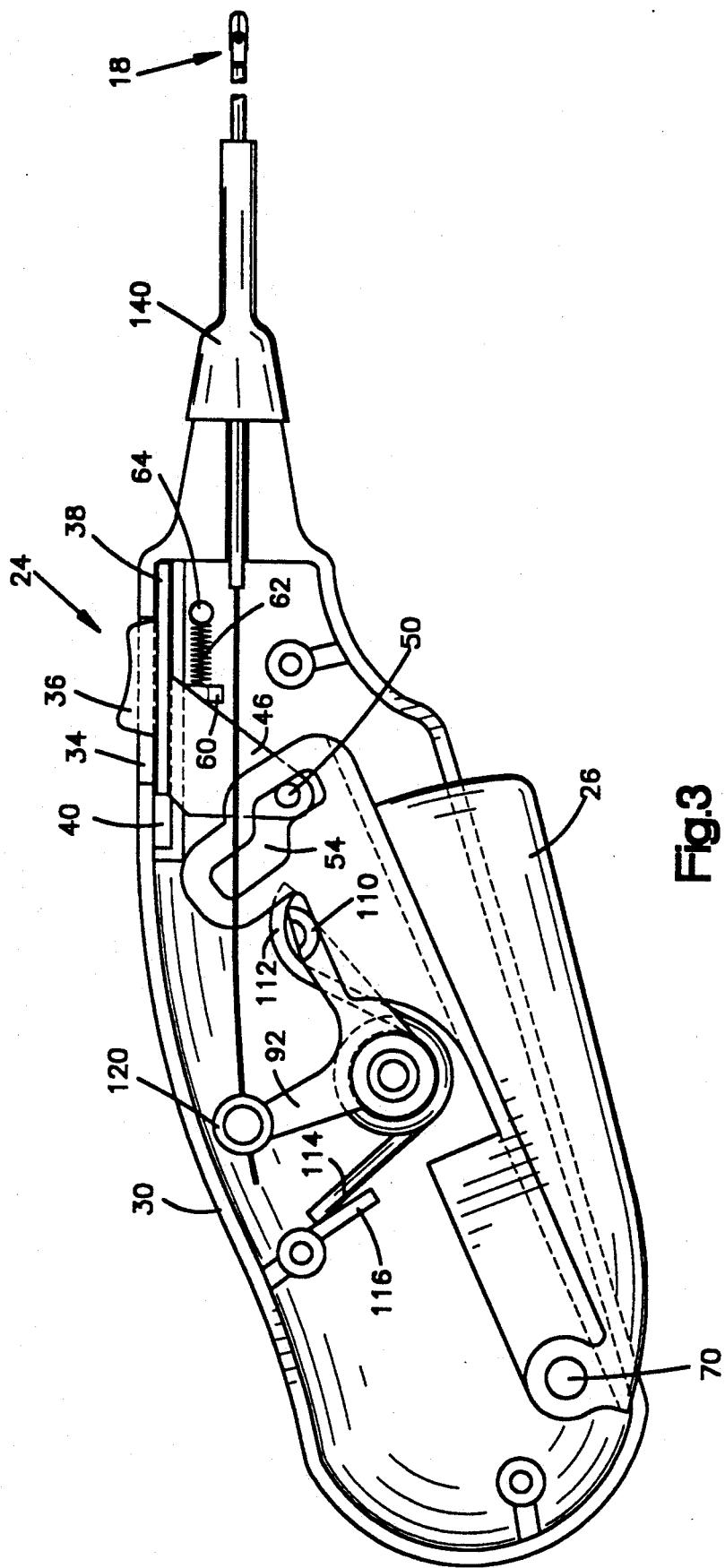
FIG. 3 is a sectional view of the device illustrated in FIGS. 1 and 2 and showing the forceps in a closed condition.
Figure 5:
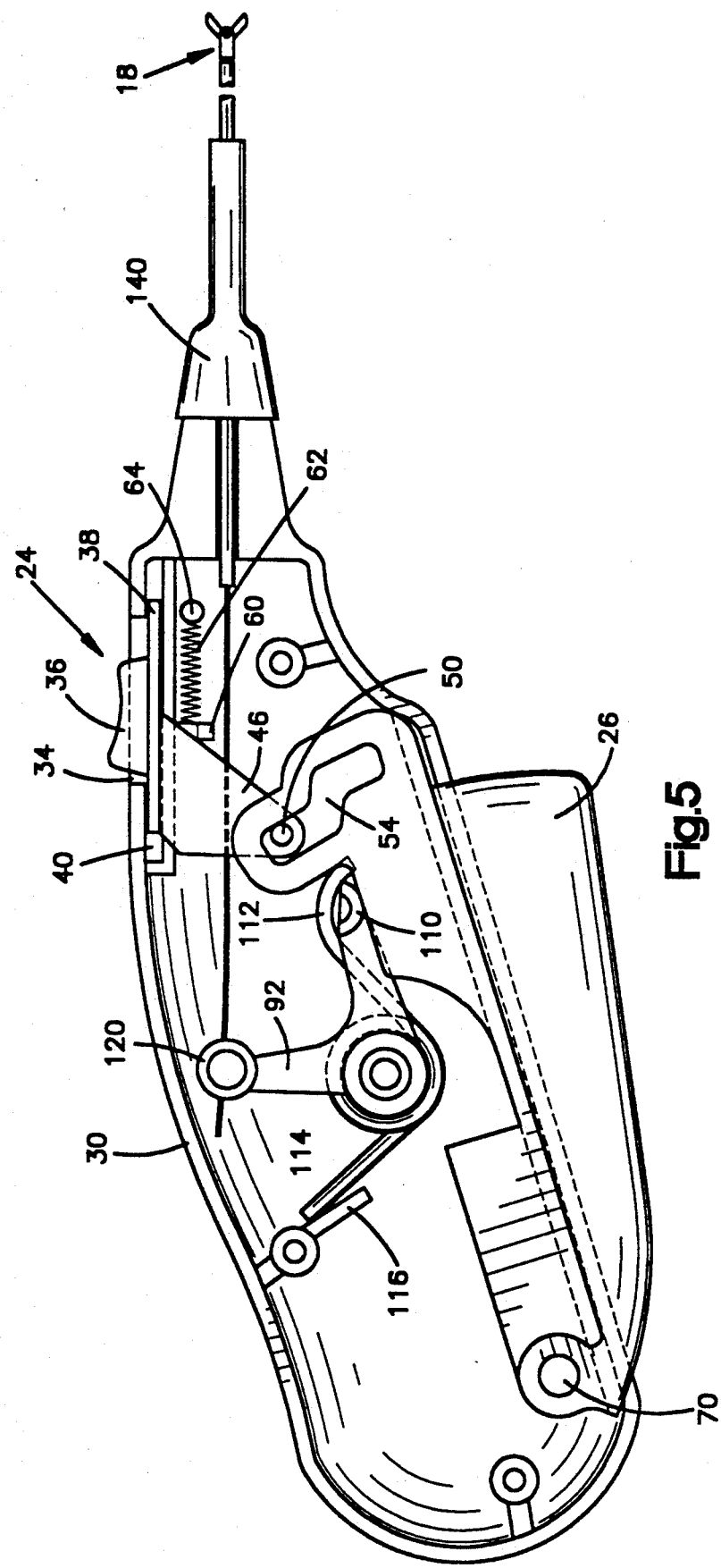
FIG. 5 is a view similar to that of FIGS. 3 and 4 but showing the operation when the forceps are in an open condition.

Reference is now made to the drawings wherein the showings are for purposes of illustrating a preferred embodiment only and not for purposes of limiting same. As shown in the drawings, there is provided a biopsy forceps device 10 which includes a handle assembly 12 and an elongated flexible hollow body taking the form of a coil spring guide 14 which extends from the distal end 16 of the handle assembly to a forceps assembly 18. The guide 14 has a lumen extending throughout its length and the lumen slidably receives a control wire 20 which is connected at its distal end to the forceps assembly 18 and secured at its proximal end to a grip 22. The guide is surrounded by a plastic protective sleeve 21. The grip 22, as will be brought out in greater detail hereinafter, displaces the control wire 20 from the proximal position, as shown in FIG. 3, forwardly to a distal position, as shown in FIG. 5, to thereby open the forceps assembly 18. As will be brought out in greater detail hereinafter, this action results from the operator engaging a trigger 24 with his thumb and pulling the trigger rearwardly from its distal position to its proximal position.

The handle 12 is of an in-line design and may be easily grasped by either hand of a physician with the thumb engaging the trigger 24 and with the fingers engaging a lever arm 26. The forceps are operated to an open condition by the physician placing his thumb on the trigger 24 and pulling back on the trigger until it locks in a proximal position. With the trigger in its proximal position, the physician may close the forceps by compressing the lever arm 26 up into the clamshell body of the handle assembly 12.

The handle assembly 12 resembles a clamshell body having a first clamshell half 30 and second clamshell half 32 which are hollowed out to receive and support the components to be described hereinbelow. The clamshell halves may be secured to each other as with suitable screws or by means of a snap fit. The distal end 16 of the handle assembly 12 is tapered in the distal direction and is provided with a passageway or lumen 31 which extends in an axial or in-line direction with the coil spring guide 14. This permits the proximal end of the coil spring guide 14 to be received by the lumen 31. The control wire 20 is slidably displaced within the lumen of guide 14 back and forth between its distal and proximal positions while opening and closing the forceps 18.

The handle assembly 12 is provided with a longitudinally extending opening 34 in its upper wall near the distal end thereof and a thumb button 36 of the trigger 24 extends upwardly and beyond the opening so that it may be easily engaged by the thumb of the operator. The thumb button 36 extends upward from a flat rectangular platform 38 and the longitudinal sides of the platform are received in tracks 40 located in the interior side walls in the cooperating clamshell halves 30 and 32 just below the opening 34. This permits the trigger 24 to slide back and forth between its distal and proximal positions. The trigger 24 is also provided with a pair of legs 44 and 46 which extend vertically downward from the underside of platform 38. At the lower end of leg 44 there is provided a transversely extending cam post 48. A similar cam post 50 extends transversely outward from the bottom of leg 46. These cam posts ride in a pair of cam tracks 52 and 54 located in the lever arm 26.

The trigger 24 has a rod-like post 60 which extends from the underside of platform 38 in a downward direction between legs 44 and 46. This post 60 (as best seen in FIG. 3) serves to anchor one end of a compression spring 62 with the other end of the compression spring being anchored to a rod-like post 64 which extends inwardly from a side wall of the clamshell half 30. This compression spring provides the resilient force that tends to keep the trigger 24 in its forward or distal position, as seen in FIG. 3.

Figure 1:
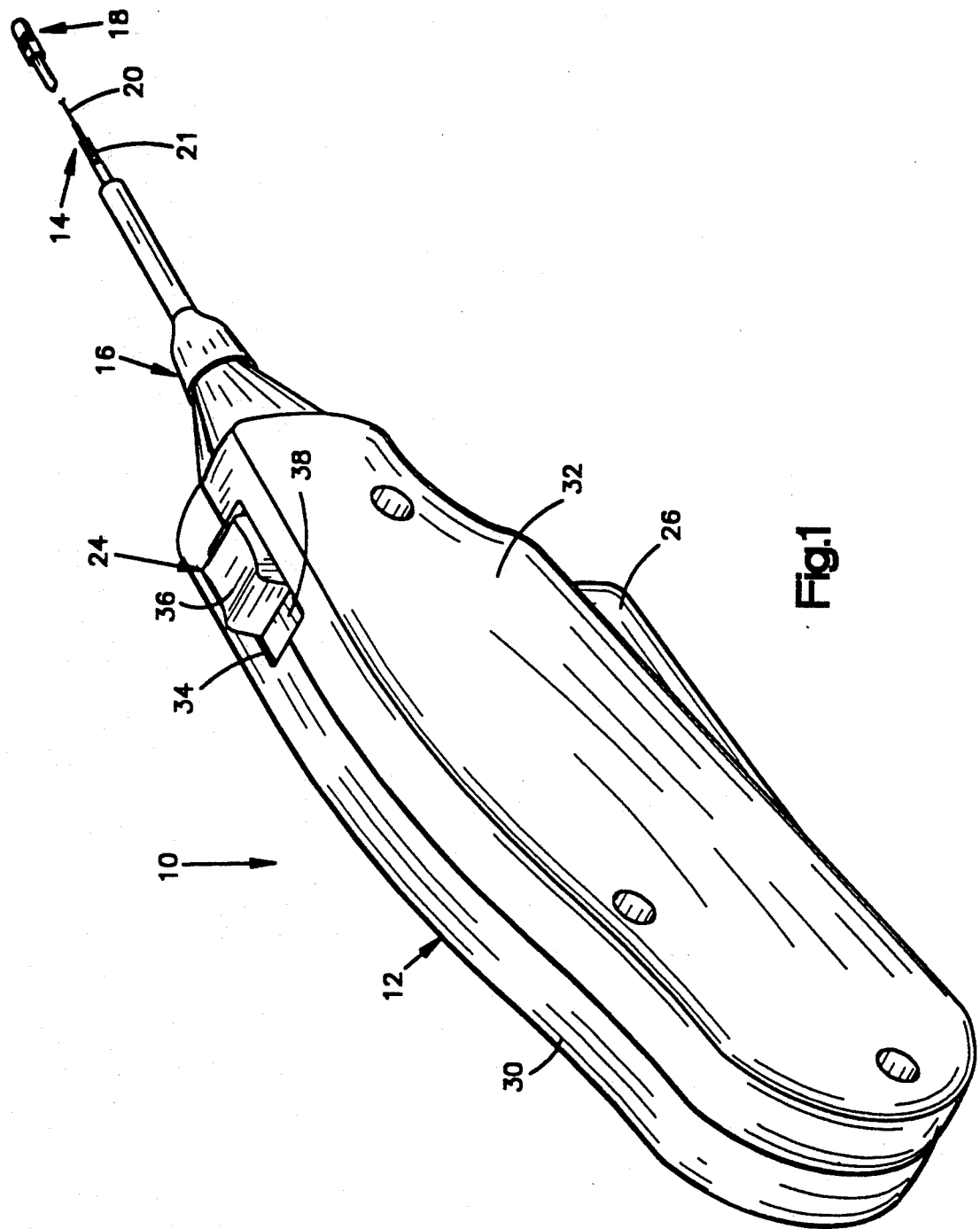
FIG. 1 is a perspective view of a biopsy forceps device.
Figure 2:
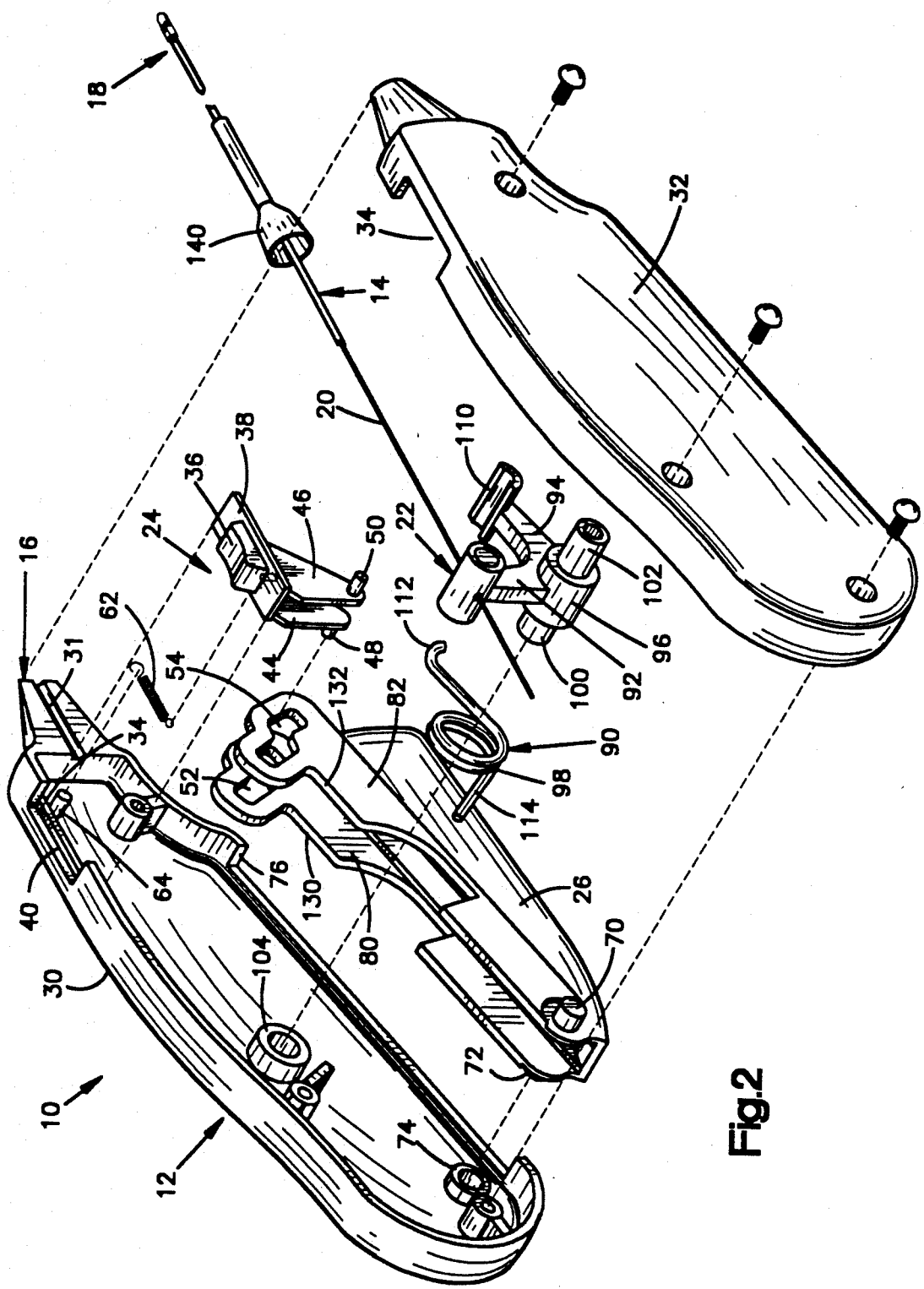
FIG. 2 is an exploded view showing various of the components employed in the device illustrated in FIG. 1.

The lever arm 26 has a pair of pivot posts 70 and 72 which extend transversely outward from the arm at one end thereof. These pivot posts are received in a pair of facing pivot sleeves 74, of which only one is seen in FIG. 2, provided on the interior walls of clamshell halves 30 and 32. These pivot sleeves face inwardly toward the arm and have internal diameters sufficient to receive the posts 70 and 72 while permitting pivotal movement of the posts in the sleeves. Thus, post 72 is received within pivot sleeve 74 so that the arm 26 may pivot about an axis extending through the pivot post while the arm is displaced in an arcuate direction into and out of the interior of the handle assembly 12. For this purpose, the handle assembly 12 includes an elongated slot 76 which extends through the lower walls of clamshell halves 30 and 32 with the slot being of sufficient width and length to receive the lever arm 26 as it is pulled up into the interior when the operator compresses the lever arm up into the clamshell body.

The lever arm 26 has a somewhat wedge-shaped body with the apex thereof being provided with the pivot posts 70 and 72. In cross section, the lever arm is somewhat U-shaped defining a trough having a pair of upstanding side walls 80 and 82 which respectively contain the lever arm cam tracks 52 and 54. These cam tracks 52 and 54 are somewhat S-shaped.

A torsion spring 90 is employed for purposes of biasing the lever arm to its fully extended position corresponding with a forceps open condition as shown in FIG. 5. Also, this biases the grip 22 in its forward or distal position. This structure and the means for accomplishing the foregoing are described in detail hereinbelow.

The grip 22 takes the form of a V-shaped structure having a pair of legs 92 and 94 and having a transversely extending hub 96 at its apex. The hub 96 is of sufficient diameter to receive a pair of turns 98 of the spring 90 while permitting rotational movement between the hub and the turns 98. A pair of pivot posts 100 and 102 extend transversely from the hub 96 and these pivot posts are each received within a pivot sleeve 104 extending inwardly from the side walls of the clamshell halves 30 and 32 (only the pivot sleeve 104 of clamshell half 30 is visible in FIG. 2). The pivot post 100 is received within the pivot sleeve 104 such that the pivot post 100 may pivot or rotate within the sleeve 104.

Figure 4:
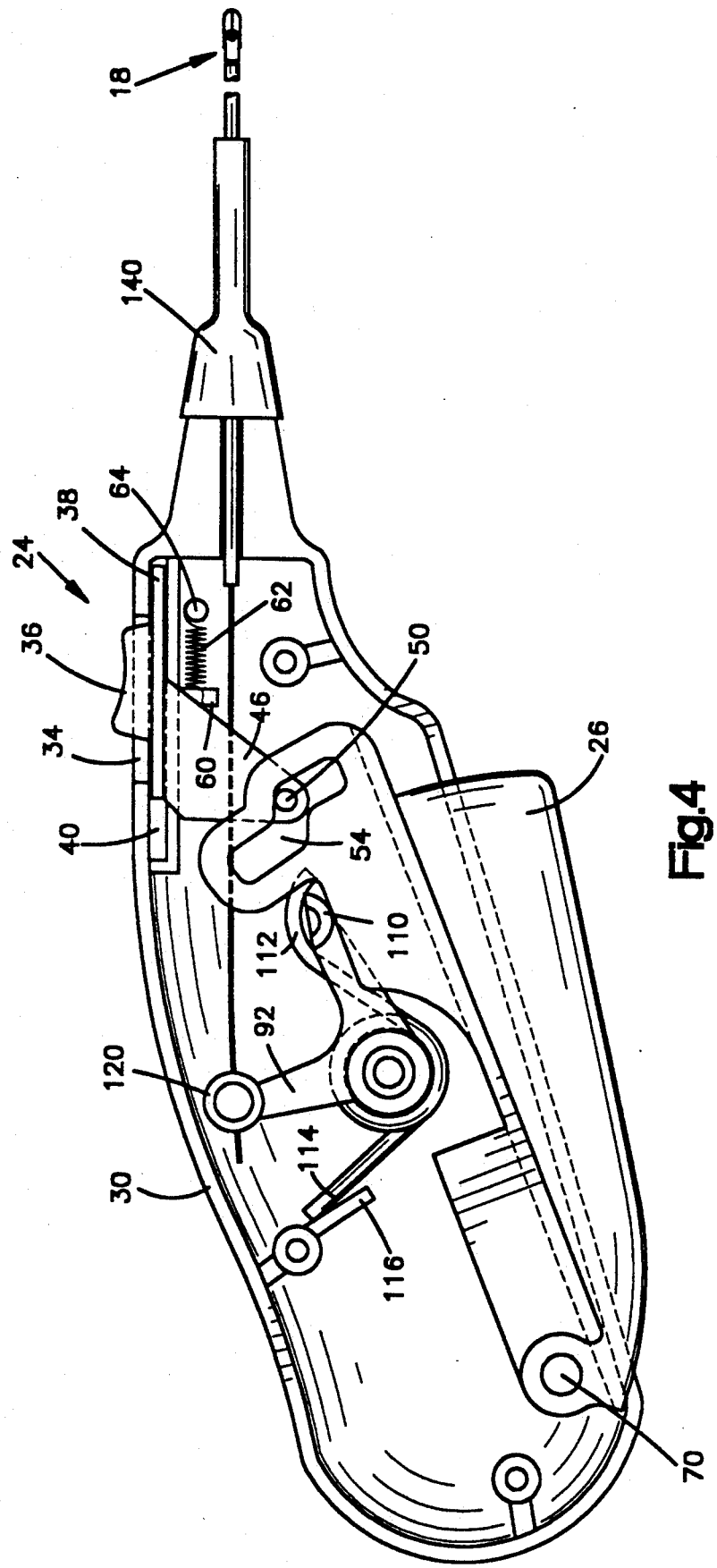
FIG. 4 is a sectional view similar to that of FIG. 3 but showing an intermediate operation condition.

Leg 94 extending from the hub 96 carries at its end a transversely extending spring retaining member 110 which receives a hooked end 112 of spring 90, as is best seen in FIGS. 3, 4 and 5. The other end 114 of spring 90 bears up against a wall 116 extending inwardly from an inner side wall of the clamshell half 30. The other leg 92 of grip 22 has a wire gripping member 120 secured to the end of the leg. This wire gripping member 120 has an aperture therein for receiving a portion of the length of the control wire 20 and which is fastened to the gripping member 120, as with a sot screw, not shown. The torsion spring 90 has its hooked end 112 hooked over the spring retaining member 110 of the grip 22. This forces member 110 to bear downwardly against the upper edges 130 and 132, respectively, of the lever arm side walls 80 and 82. With the other end 114 of the spring bearing against wall 116, this torsion spring biases the lever arm toward its fully extended position, shown in FIG. 5 and which corresponds with the forceps open condition. A protective plastic cover 140 extends over a portion of the distal end 16 of the handle as well as over a portion of the length of the coil spring guide 14.

In operation, the physician may grasp the handle assembly 12 in either hand and then place his thumb on the thumb button 36 and pull the button back, from its distal position to its proximal position. This action will cause the cam tracks 52 and 54 to ride down on the cam posts 48 and 50, respectively, as the lever arm pivots about its pivot posts 70 and 72 in a clockwise direction under the urging of the torsion spring 90. This action continues from the position as shown in FIG. 3, through an intermediate position, as shown in FIG. 4, and to a final position, as shown in FIG. 5 at which the forceps assembly is in its open condition. During this operation, the lever arm 26 pivots from its fully retracted position, as shown in FIG. 3, to an intermediate position, as shown in FIG. 4, and then to its fully extended position, as shown in FIG. 5. During this operation, the grip 22 is biased by the spring 90 so as to pivot in a clockwise direction causing the control wire 20 to be displaced in a distal direction sufficient to cause the forceps assembly to be actuated into its open condition. The forceps assembly is now maintained in its open condition by the resilient force exerted by spring 90.

To close the jaws, the physician compresses the lever arm 26 up into the clamshell body from the position as shown in FIG. 5 through an intermediate position as shown in FIG. 4 to the lever arm fully retracted position of FIG. 3. During this operation, the trigger 24 is released from its proximal position, as shown in FIG. 5, to travel forwardly through an intermediate position, as shown in FIG. 4, to its distal position, as shown in FIG. 3, as the platform 38 slides forwardly in a distal direction in the guides 40 within the handle (see FIG. 3). During this operation, the cam posts 48 and 50 ride in the lever arm cam tracks 52 and 54 from the position shown in FIG. 5 through that as shown in FIG. 4 and then to the position as is shown in FIG. 3 with the lever arm 26 being fully retracted into the clamshell body. As the lever arm 26 is compressed into the clamshell body, the grip 22 pivots in a counterclockwise direction about its pivot axis against the resisting force of the spring 90 during which the control wire 20 is displaced from its distal position to its proximal position sufficient to cause the forceps assembly 18 to a closed condition. In this condition, the trigger assembly 24 is held in its distal position by the force exerted by compression spring 62. The biopsy forceps is now in condition to repeat the foregoing operation by the physician applying his thumb to pull back on the thumb button on the trigger 24 in order to open the forceps assembly.

Improved Core Wire

Reference is now made to FIGS. 6 and 7 which illustrate portions of the length of the core wire 20 and its surrounding spring guide 14 in greater detail. FIG. 6 illustrates a portion of the length of the guide 14 from a point intermediate its length and then in a distal direction terminating at its coupling with a forceps assembly 18. It is to be noted that the spring guide 14 together with its core wire 20, encased within, are provided with a preset curve 200. The preset curve is formed into a shape exhibiting the most optimum curve in which a physician may gain access through the RA crossing the tricuspid valve, transverse RV to the septum wall biopsy site, for example. In accordance with the present invention, the core wire is more formable in the area approaching the distal end thereof to permit the physician to increase or decrease the curvature of the preset curve 200, as desired. The core wire exhibits greater torque and pushability characteristics in the area close to the proximal end thereof to facilitate the physician's advancing the biopsy device to the site of interest.

The core wire 20 is divided into at least three, but preferably four, distinct portions, including a distal portion 20A, a first intermediate portion 20B, a second intermediate portion 20C and a proximal portion 20D. The proximal end 202 of proximal portion 20D is fixed to a control wire displacing means taking the form of grip 22 which, as described hereinbefore, is mounted to the handle assembly and serves to move the core wire 20 between a forceps open position and a forceps closed position. Other suitable means may be employed for displacing the core wire between these two positions.

The core wire 20 is preferably a drawn stainless steel rod having a circular cross section but having different diameters at portions 20A, 20B, 20C and 20D. That is, portion 20D has a diameter greater than that of portion 20C, which, in turn, has a greater diameter than that of portion 20B and which, in turn, has a diameter greater than that of portion 20A. Moreover, these portions have different lengths, with the proximal portion 20D having a length greater than that of the second intermediate portion 20C, and which, in turn, has a length greater than that of the first intermediate portion 20B, and which, in turn, has a length greater than that of the distal portion 20A. For example, for a core wire having a length of 32.50 inches, the distal portion 20A may have a length on the order of $2.25 \pm 0.10$ inches and a diameter on the order of $0.0190 \pm 0.0003$ inches. The first intermediate portion 20B may have a length on the order of $2.50 \pm 0.10$ inches and a diameter on the order of $0.0230 \pm 0.0003$ inches. Also, the second intermediate portion 20C may have a length on the order of $6.00 \pm 0.10$ inch and a diameter on the order of $0.0250 \pm 0.0003$ inches. Lastly, the proximal portion 20D may have a length on the order of $17.25 \pm 0.10$ inch and a diameter on the order of $0.0270 \pm 0.0007$ inches.

The core wire 20 has three tapered portions including a first tapered portion 204, a second tapered portion 206 and a third tapered portion 208. The first tapered portion 208 is located intermediate the distal portion 20A and the first intermediate portion 20B and has a length on the order of $1.00 \pm 0.10$ inch. The second tapered portion 206 is located intermediate the first intermediate portion 20B and the second intermediate portion 20C and has a length on the order of $1.50 \pm 0.10$ inch. Lastly, the third tapered portion 208 is located intermediate the second intermediate portion 20C and the proximal portion 20D and has a length on the order of 2.00±0.10 inch. Each tapered portion has a taper that extends inwardly in the distal direction. The first tapered portion 204 exhibits a first tapered angle Φ1 which is greater than the tapered angle Φ2 of the second tapered portion 206 and which, in turn, is greater than the tapered angle Φ3 of the third tapered portion 208.

The foregoing dimensions are chosen to provide relative lengths, diameters and tapered angles to permit the structure to exhibit maximum pushability and torqueability at the proximal portion 20D. The dimensions for the second intermediate portion 20C provide sufficient cross sectional area to transmit the torque needed to steer portions 20A and 20B through the heart valves to the septum wall. The first intermediate portion 20B provides a location to commence the preset curve 200 so that the curve in the wire is somewhat uniform throughout this portion. Portion 20A provides substantially greater flexibility than the other portions permitting additional curvature, as desired by the physician, to the preset curve 200, while also providing a distal portion that is flexible and formable to deter perforation. The core wire offers optimum torque transmission, distal formability and flexibility while maintaining a core wire having a diameter less than 0.030 inches. Moreover, by providing the step-down diameters along portions extending toward the distal end, a core wire has been provided that exhibits excellent torqueability and pushability while yet maintaining formability and flexibility in the area of the distal end.

Although the invention has been described in conjunction with a preferred embodiment, it is to be appreciated that various modifications may be made without departing from the spirit and scope of the invention as defined by the appended claims.

Having described the invention, the following is claimed:

1. A biopsy forceps device comprising:
   a handle;
   an elongated flexible hollow-body portion having a lumen extending therethrough, and having a proximal end and a distal end;
   a forceps assembly coupled to the distal end of said body portion, and including a pair of forceps;
   control wire means having proximal and distal ends, and extending through the lumen is said body portion and coupled at its distal end to a said forceps assembly;
   control wire displacing means carried by said handle and secured to the proximal end of said control wire means and movable between first and second positions for respectively moving said control wire means between a forceps open position and a forceps closed position;
   said control wire means including an elongated metal rod having at least three portions including a proximal portion having a proximal end secured to said wire displacing means, a distal portion having a distal end secured to said forceps assembly and an intermediate portion located intermediate said proximal and said distal portions;
   said proximal portion being of greater length than either said intermediate or distal portions;
   said proximal portion being of greater diameter than said intermediate portion and wherein said intermediate portion has a diameter greater than that of said distal portion;
   first and second tapered portions each having a taper which tapers inwardly in the distal direction; and
   said first tapered portion being intermediate said distal portion and said intermediate portion, and said second tapered portion being intermediate said intermediate portion and said proximal portion.

2. A biopsy forceps device as set forth in claim 1 wherein said intermediate portion is of greater length than that of said distal portion.

3. A biopsy forceps device as set forth in claim 2 wherein said first and second tapered portions taper inwardly by first and second tapered angles, respectively, and wherein said first tapered angle is greater than said second tapered angle.

4. A biopsy forceps device as set forth in claim 2 wherein said second tapered portion is of greater length than said first tapered portion.

5. A biopsy forceps device as set forth in claim 1 wherein said intermediate portion is a first intermediate portion, and wherein said control wire means includes a second intermediate portion which is intermediate said first intermediate portion and said proximal portion.

6. A biopsy forceps device as set forth in claim 5 wherein the length of said proximal portion is greater than the length of said second intermediate portion and which, in turn, is greater than the length of said first intermediate portion and which, in turn, is greater than the length of said distal portion.

7. A biopsy forceps device as set forth in claim 1 including a third tapered portion, and wherein said first tapered portion is intermediate said distal portion and said first intermediate portion, said second tapered portion is intermediate said first intermediate portion and said second intermediate portion, and wherein said third tapered portion is intermediate said second intermediate portion and said proximal portion.

8. A biopsy forceps device as set forth in claim 7 wherein said first, second, and third tapered portions respectively taper inwardly by first, second, and third tapered angles respectively, and wherein said first tapered angle is greater than that of said second tapered angle, and wherein said second tapered angle is greater than that of said third tapered angle.

9. A biopsy forceps device as set forth in claim 8 wherein said third tapered portion has a length greater than that of said second tapered portion and which, in turn, has a length greater than that of said first tapered portion.

10. A biopsy forceps device as set forth in claim 1 wherein said control wire has a preset curve in said distal portion and wherein said distal portion is sufficiently formable that the curvature of said preset curve may be manually varied.

11. A biopsy forceps device comprising:
    a handle;
    an elongated flexible hollow-body portion having a lumen extending therethrough, and having a proximal end and a distal end;
    a forceps assembly coupled to the distal end of said body portion, and including a pair of forceps;
    control wire means having proximal and distal ends, and extending through the lumen in said body portion and coupled at its proximal end to said handle and at its distal end to said forceps assembly;
    control wire displacing means carried by said handle and secured to the proximal end of said control wire means and movable between first and second positions for respectively moving said control wire means between a forceps open position and a forceps closed position;

said control wire means including an elongated metal rod including a proximal portion having a proximal end secured to said wire displacing means and a distal portion having a distal end secured to said forceps assembly;

said control wire being constructed such that said proximal end is of greater diameter than said distal end whereby said control wire exhibits greater torqueability and pushability at its proximal end than at its distal end and exhibits greater flexibility and formability at its distal end than at its proximal end.

12. A biopsy forceps device as set forth in claim 11 wherein said control wire has a preset curve in said distal portion and wherein said distal portion is sufficiently formable that the curvature of said preset curve may be manually varied.

13. A biopsy forceps device as set forth in claim 12 wherein said control wire means further includes an intermediate portion located intermediate said proximal and said distal portions.

14. A biopsy forceps device as set forth in claim 13 wherein said proximal portion has a diameter greater than that of said intermediate portion and wherein said intermediate portion has a diameter greater than that of said distal portion.

15. A biopsy forceps device as set forth in claim 14 wherein said proximal portion is of greater length than said intermediate portion and wherein said intermediate portion is of greater length than that of said distal portion.

* * * * *